US00PP20318P3

(12) United States Plant Patent
Noodelijk

(10) Patent No.: US PP20,318 P3
(45) Date of Patent: Sep. 15, 2009

(54) ***CHRYSANTHEMUM* PLANT NAMED 'PETNO ORANGE'**

(50) Latin Name: *Chrysanthemum morifolium*
Varietal Denomination: Petno Orange

(76) Inventor: Robert Noodelijk, Vrouwgeestweg 26, Woubrugge (NL), 2481 KN ( * ) Notice: Subject to any disclaimer, the term of this patent is extended or adjusted under 35 U.S.C. 154(b) by 52 days.

(21) Appl. No.: 12/002,183

(22) Filed: Dec. 14, 2007

(65) Prior Publication Data

US 2009/0158482 P1 Jun. 18, 2009

(51) Int. Cl.
*A01H 5/00* (2006.01)

(52) U.S. Cl. ..... Plt./296

(58) Field of Classification Search ..... Plt./286, Plt./296

See application file for complete search history.

*Primary Examiner*—Susan B McCormick Ewoldt
(74) *Attorney, Agent, or Firm*—Jondle & Associates, P.C.

(57) ABSTRACT

A *chrysanthemum* plant named 'Petno Orange' characterized by small-sized orange flowers with yellow-green centers, prolific branching, a natural season flowering date of 26 September, a blooming period of 6 weeks, a round to flat plant habit, a spreading growth habit and rapid growth rate, is disclosed.

1 Drawing Sheet

Genus: *Chrysanthemum morifolium.*
Variety denomination: 'Petno Orange'.

BACKGROUND OF THE INVENTION

'Petno Orange' is a product of a breeding and selection program for outdoor pot mums (garden mums) which had the objective of creating new *chrysanthemum* cultivars with a decorative type flower, a natural season flowering date around September 26 and a blooming period of 6 weeks. The new plant of the present invention comprises a new and distinct cultivar of *chrysanthemum* plant.

'Petno Orange' is a seedling resulting from the open pollination among groups of un-named, unknown and unpatented *chrysanthemum* cultivars maintained under the control of the inventor for breeding purposes. The new and distinct cultivar was discovered and selected as one flowering plant by Rob Noodelijk on a cultivated field in Woubrugge, The Netherlands in September 2005. The plant has been asexually reproduced by cuttings in greenhouses at Woubrugge, The Netherlands over a two year period. The new cultivar has been found to retain its distinctive characteristics through successive propagations.

SUMMARY OF THE INVENTION

The following are the most outstanding and distinguishing characteristics of the new cultivar when grown under normal horticultural practices in Woubrugge, The Netherlands.

1. Small, double orange flowers with yellow-green centers;
2. Prolific branching;
3. A rounded to flat plant habit; and
4. A spreading growth habit and rapid growth rate.

DESCRIPTION OF THE PHOTOGRAPHS

The present invention of a new and distinct variety of *chrysanthemum* is shown in the accompanying photographs, the colors being as nearly true as possible with color photographs of this type.

DESCRIPTION OF THE INVENTION

Figure 1:
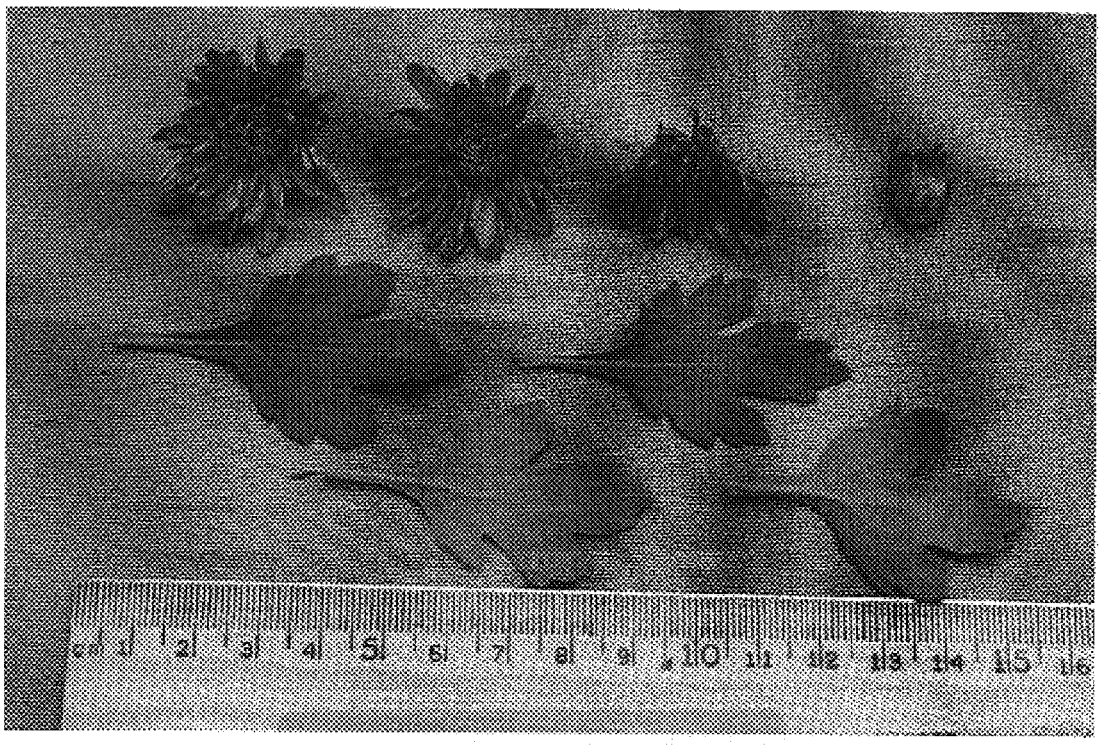
FIG. 1 shows a close-up of the individual flowers, bud and leaves.
Figure 2:
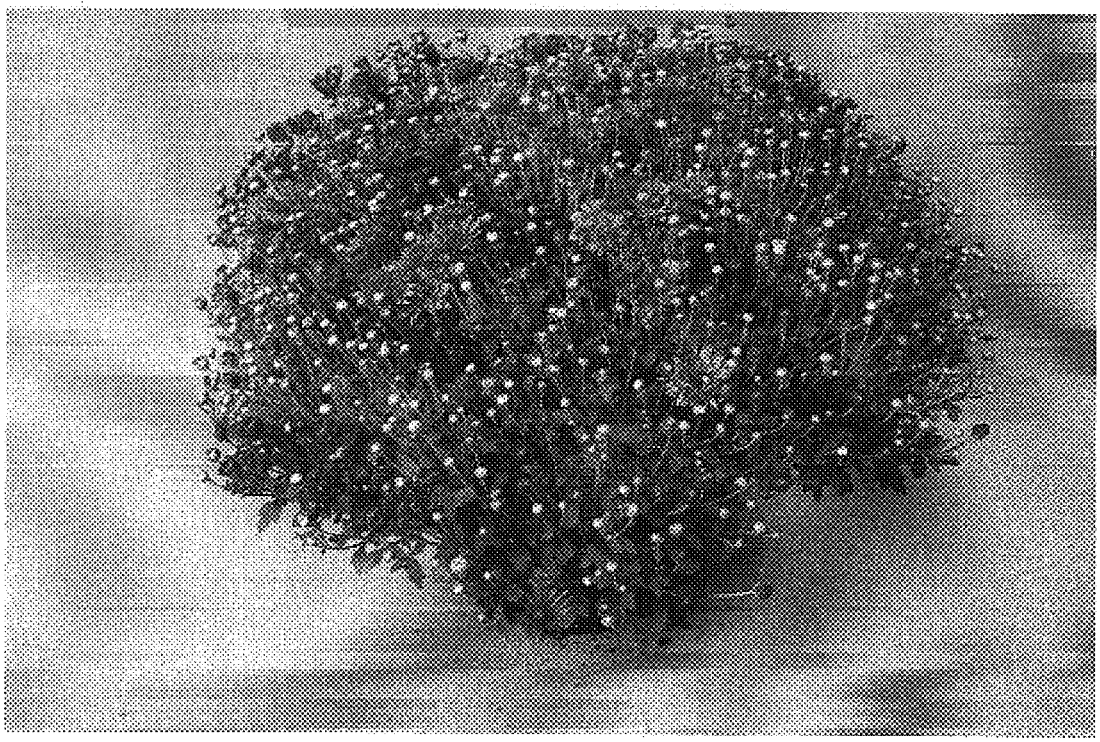
FIG. 2 shows a plant of the cultivar in full bloom.

This new variety of *chrysanthemum* is of the botanical classification *Chrysanthemum morifolium.* The observations and measurements were gathered from plants grown outdoors in Woubrugge, The Netherlands under natural day length and temperature and planted in week 22 in 2005 and 2006. The natural blooming date of this crop was September 26. The average height of the plants was 42 cm. No growth retardants were used. No tests were done on disease or insect resistance or susceptibility. No tests were done on cold or drought tolerance. This new variety produces small-sized blooms with orange ray florets and small yellow-green centers and a blooming period of 6 weeks.

The following is a description of the plant and characteristics that distinguish 'Petno Orange' as a new and distinct variety. The color designations are taken from the plant itself. Accordingly, any discrepancies between the color designations and the colors depicted in the photographs are due to photographic tolerances. The color chart used in this description is The Royal Horticultural Society Colour Chart, edition 1995.

BOTANICAL DESCRIPTION OF 'PETNO ORANGE'

Plant:

*Shape.*—Rounded to flat.
*Growth habit.*—Spreading.
*Growth rate.*—Rapid.
*Height.*—42 cm to 46 cm.
*Width.*—48 cm to 50 cm.

Branches:

*Stem color.*—RHS 137C (green).

*Stem.*—Strength: Strong. Brittleness: Absent. Anthocyanin Coloration: Present, a slight layer of RHS 181A (greyed-red) mainly at the base of the stem.

*Length of lateral branch* (*from top to bottom*).—17 cm to 15 cm.

*Lateral branch color.*—RHS 137C (green).

*Lateral branch attachment.*—Petiolate.

*Branching* (*average number of lateral branches*).—Very prolific with 11 breaks after pinching.

Leaves:

*Color.*—Upper surface: RHS 146A (yellow-green). Lower surface: RHS 137C (green).

*Size.*—General: Medium. Length: 4.3 cm to 4.5 cm. Width: 3.3 cm to 3.5 cm.

*Quantity* (*number per lateral branch*).—7 to 8.

*Shape.*—Obovate to round.

*Apex.*—Acute.

*Base.*—Asymmetric.

*Margin.*—Crenate.

*Texture.*—Upper surface: Glabrous. Lower surface: Pubescent.

*Venation arrangement.*—Palmate.

*Shape of base of sinus between lateral lobes.*—Acute.

*Margin of sinus between lateral lobes.*—Diverging.

Bud:

*Size.*—General: Medium. Cross-section: 1.5 cm. Height: 1.5 cm.

*Outside color.*—RHS 172A (greyed-orange).

*Involucral bracts.*—2 rows, length 0.7 cm, width 0.3 cm.

*Involucral bracts among disc-florets.*—Absent.

*Involucral bracts color.*—RHS 138A (green).

Bloom:

*Type.*—Double.

*Size.*—General: Small. Fully expanded: 3.7 cm to 4.0 cm.

*Number of blooms per branch.*—Approximately 7 blooms per branch.

*Performance on the plant* (*blooming period*).—6 weeks.

*Fragrance.*—Typical *chrysanthemum*, slight.

*Tonality from distance.*—A rich flowering garden mum with small orange flowers and a small green disc.

*Discoloration to color.*—None.

*Peduncle.*—Length: 9 cm to 10 cm. Color: RHS 137C (green).

*Natural season blooming date.*—26 September.

Ray florets:

*Texture.*—Both the upper and lower surfaces are smooth.

*Number.*—110 to 130.

*Cross-section.*—Concave.

*Longitudinal axis of majority.*—Flat to incurved.

*Length of corolla tube.*—0.3 cm.

*Apex.*—Rounded.

*Margin.*—Entire.

*Length.*—1.5 cm to 1.7 cm.

*Width.*—0.3 cm to 0.5 cm.

*Ratio length/width.*—High.

*Color.*—Upper surface of the outer ray-florets: Near RHS 172C (greyed-orange). Lower surface of the ray-florets: Near RHS 167C (greyed-orange).

Disc florets:

*Disc diameter.*—0.4 cm.

*Distribution of disc florets.*—A few, visible at all stages of flowering.

*Shape.*—Funnel-shaped.

*Color.*—RHS 151A (yellow-green).

*Receptacle shape.*—Domed flat.

*Color of center of the flower* (*disc-florets*).—Immature: RHS 151A (yellow-green). Mature: RHS 151A (yellow-green).

Reproductive organs:

*Stamen* (*present in disc florets only*).—Absent.

*Pollen.*—Absent.

*Styles.*—Thin.

*Style color.*—RHS 144A (yellow-green).

*Style length.*—0.3 cm to 0.4 cm.

*Stigma color.*—RHS 144A (yellow-green).

*Stigma width.*—0.1 cm.

*Ovaries.*—Enclosed in calyx.

Fruit/seed set: Seeds are produced in small quantities; ovate, RHS 199A (grey-brown) and 0.15 cm in length.

COMPARISON WITH COMMERCIAL CULTIVARS

'Petno Orange' differs from the commercial cultivar 'Spicy Yocheryl' (U.S. Plant Pat. No. 13,221) in that 'Petno Orange' flowers earlier (September 26) than 'Spicy Yocheryl' (October 6). 'Petno Orange' has orange double flowers with yellow-green centers, while 'Spicy Yocheryl' has pale orange flowers. Additionally, 'Petno Orange' is more vigorous than 'Spicy Yocheryl'.

'Petno Orange' differs from the commercial cultivar 'Yomiranda' (U.S. Plant Pat. No. 16,848) in that 'Petno Orange' has a later flowering date (September 26) than 'Yomiranda' (September 22). Additionally, 'Petno Orange' has orange double flowers with yellow-green centers and has high vigor, while 'Yomiranda' has pale orange to almost apricot-colored flowers and has moderate vigor.

I claim:

1. A new and distinct variety of *chrysanthemum* plant as described and illustrated.

* * * * *